(12) United States Patent
Osypka

(10) Patent No.: US 7,909,798 B2  
(45) Date of Patent: Mar. 22, 2011

(54) PEEL-AWAY INTRODUCER SHEATH HAVING PITCHED PEEL LINES AND METHOD OF MAKING SAME

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 34 days.

(21) Appl. No.: 12/220,378

(22) Filed: Jul. 24, 2008

(65) Prior Publication Data

US 2009/0030374 A1    Jan. 29, 2009

Related U.S. Application Data

(60) Provisional application No. 60/961,856, filed on Jul. 25, 2007.

(51) Int. Cl.
*A61M 5/178* (2006.01)

(52) U.S. Cl. .................................. 604/164.05; 604/161

(58) Field of Classification Search ............. 604/164.05, 604/93.01, 164.01, 164.08, 171, 43, 160, 604/161, 264; 600/114; 606/108
See application file for complete search history.

(56) References Cited

U.S. PATENT DOCUMENTS

| | | | |
|---|---|---|---|
| 4,166,469 A | 9/1979 | Littleford | |
| 4,243,050 A | 1/1981 | Littleford | |
| 4,345,606 A | 8/1982 | Littleford | |
| 4,512,351 A | 4/1985 | Pohndorf | |
| 4,687,469 A | 8/1987 | Osypka et al. | |
| 4,776,846 A | 10/1988 | Wells | |
| 4,883,468 A | 11/1989 | Kousai et al. | |
| 4,952,359 A | 8/1990 | Wells | |
| 5,180,372 A | 1/1993 | Vegoe et al. | |
| 6,494,860 B2 | 12/2002 | Rocamora et al. | |
| 6,599,237 B1 * | 7/2003 | Singh | 600/114 |
| 6,641,564 B1 * | 11/2003 | Kraus | 604/164.1 |
| 6,939,327 B2 * | 9/2005 | Hall et al. | 604/164.05 |
| 7,192,433 B2 | 3/2007 | Osypka et al. | |
| 2004/0181188 A1 * | 9/2004 | Schaer et al. | 604/95.04 |
| 2008/0208128 A1 * | 8/2008 | Guo et al. | 604/164.05 |

* cited by examiner

*Primary Examiner* — Nicholas D Lucchesi  
*Assistant Examiner* — Brooke M Matney  
(74) *Attorney, Agent, or Firm* — Scott D. Wofsy; Edwards Angell Palmer & Dodge LLP

(57) ABSTRACT

A percutaneous peel-away vascular introducer that includes an elongated tubular sheath having opposed proximal and distal ends, and a pair of diametrically opposed peel lines that extend along the length of the sheath from the proximal end thereof to the distal end thereof, wherein the diametrically opposed peel lines have an axially extending pitch. The introducer further includes a pair of spreadable handles associated with the proximal end of the sheath for splitting the sheath along the peel lines.

14 Claims, 2 Drawing Sheets

PEEL-AWAY INTRODUCER SHEATH HAVING PITCHED PEEL LINES AND METHOD OF MAKING SAME

CROSS-REFERENCE TO RELATED APPLICATION

This application claims priority to U.S. Provisional Patent Application No. 60/961,856, filed Jul. 25, 2007, which is incorporated herein by reference.

BACKGROUND

The subject technology relates to a vascular introducer, and more particularly, to a vascular introducer having a peel-away sheath with pitched peel lines and to a method of forming the same by way of extrusion.

Introducer devices have been employed for inserting catheters, guide wires, leads and the like into patients. A typical procedure provides for insertion of a dilator or needle encased within a sheath into the vasculature of a patient. After insertion, the dilator or needle may be removed leaving the sheath protruding from the patient's vein. The sheath is then removed. To remove the sheath, the sheath may be split or peeled away along two diametrically opposed score lines. Alternatively, the sheath may be slit open using a specialized cutting blade.

Examples of splittable or peelable introducer sheaths are shown in U.S. Pat. No. 6,494,860 to Rocamora et al. and U.S. Pat. No. 7,192,433 to Osypka et al., the disclosures of which are herein incorporated by reference in their entireties. Typically, splittable introducer sheaths are prepared by forming straight score lines along the length of the sheath using a mandrel. An example of a device for slitting an introducer sheath is disclosed in U.S. Pat. No. 4,687,469 to Osypka, the disclosure of which is also incorporated herein by reference in its entirety. Typical slitter devices include a body or handle portion with a cutting edge or knife secured thereto such that the cutting edge may be manually guided to cut the sheath.

SUMMARY OF THE INVENTION

There are drawbacks associated with peelable sheaths and slitting devices. On one hand, peelable sheaths with straight score lines do not evenly distribute the shearing forces during peeling. This can make operation difficult or even result in malfunction such as partial or uneven separation. As for slitting devices, the expense of providing a separate device can be significant. Additionally, the manual dexterity required to operate a slitter can be undesirably high. There is a need, therefore, for an improved sheath which evenly distributes sheering forces, is efficient to fabricate and easy to use as well as assuring adequate separation.

The subject technology is directed to a new and useful percutaneous peel-away vascular introducer that includes an elongated tubular sheath having opposed proximal and distal ends, and a pair of diametrically opposed peel lines that extend along the length of the sheath from the proximal end thereof to the distal end thereof, wherein the diametrically opposed peel lines have an axially extending pitch. The introducer further includes a pair of spreadable handles associated with the proximal end of the sheath for splitting the sheath along the peel lines.

Preferably, the axially extending pitch of the peel lines is between about 5° and 45°. The opposed peel lines are defined by axially extending regions of reduced wall thickness, relative to the wall thickness of the remainder of the sheath. Each axially extending region of reduced wall thickness is preferably defined by a concave or flattened outer wall surface and a corresponding concave inner wall surface. Preferably, the radius of curvature of the concave inner wall surface is greater than the radius of curvature of the concave outer wall surface.

In accordance with a preferred embodiment of the subject technology, the tubular introducer sheath is formed from a polymeric material in an extrusion process. The polymeric material may be a block copolymer such as Pebax® copolymer available from Arkema of Colombes, France. The block copolymer material is fed through a unique die while an extruding machine imparts a controlled rotation to the material. This rotation causes a gradual pitch of the peel lines.

In accordance with another preferred embodiment of the subject technology, a peel-away vascular introducer includes an elongated tubular sheath having opposed proximal and distal ends, and a pair of opposing peel lines extending from the proximal end thereof to the distal end thereof, wherein the opposed peel lines at least partially extend around an axis of the sheath. The peel-away vascular introducer may include spreadable handles associated with the proximal end of the sheath for splitting the sheath along the peel lines.

In accordance with still another preferred embodiment of the subject technology, a method of forming a tubular sheath for an introducer assembly includes the steps of forming a tubular structure in an extrusion process and forming opposed peel lines in the tubular structure, wherein the peel lines have an axially extending pitch. The method may include the step of forcing a molten polymeric extrudate through a die in a rotating motion to create the pitch, wherein a continuously rotating mixer is used to create the rotating motion.

These and other features of the subject invention will become more readily apparent to those skilled in the art from the following detailed description of the preferred embodiment taken in conjunction with the drawings.

BRIEF DESCRIPTION OF THE DRAWINGS

So that those skilled in the art to which the subject invention appertains will readily understand how to make and use the subject invention without undue experimentation, preferred embodiments thereof will be described in detail hereinbelow with reference to certain figures, wherein.

DETAILED DESCRIPTION OF PREFERRED EMBODIMENTS

Figure 1:
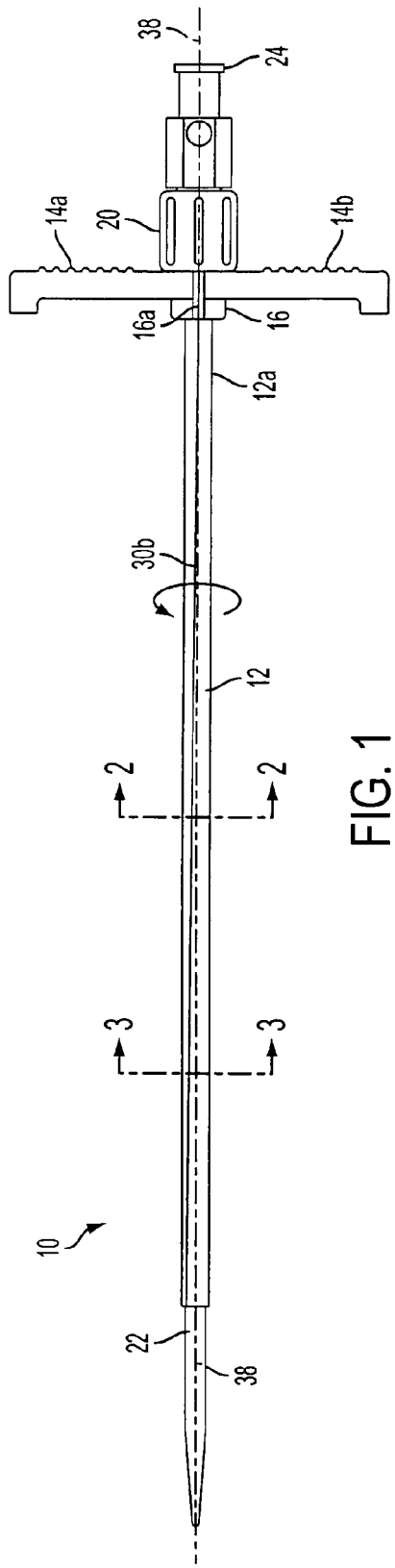
FIG. 1 is a side elevational view of a percutaneous introducer constructed in accordance with a preferred embodiment of the subject technology, which includes pitched peel lines for splitting the introducer sheath.

The present disclosure overcomes many of the prior art problems associated with removing introducer sheaths. The advantages, and other features of the technology disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Referring now to FIG. 1, there is illustrated a vascular introducer assembly 10 that includes an elongated tubular sheath 12 defining opposed proximal and distal end portions 12a, 12b. A handle assembly 14 is operatively associated with the proximal end portion 12a of the tubular sheath 12. The handle assembly 14 includes a central hub 16 with a central parting line 16a defining a pair of opposed radially outwardly extending spreadable/separable handles 14a, 14b.

The introducer assembly 10 further includes an elongated dilator 20 having a tapered distal end portion 22 and a proximal leur lock fitting 24. While not shown herein, the central hub 16 of the handle assembly 14 is adapted and configured to threadably receive the dilator 20, as disclosed in U.S. Pat. No. 7,192,433, which is incorporated herein by reference.

Figure 3:
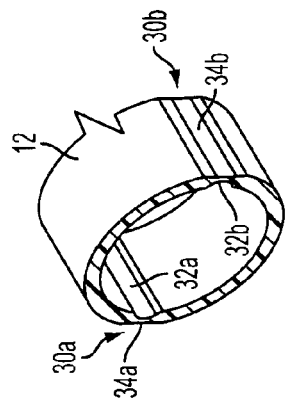
FIG. 3 is a perspective view of an axial section of the peel-away introducer sheath taken along line 3-3 of FIG. 1.
Figure 2:
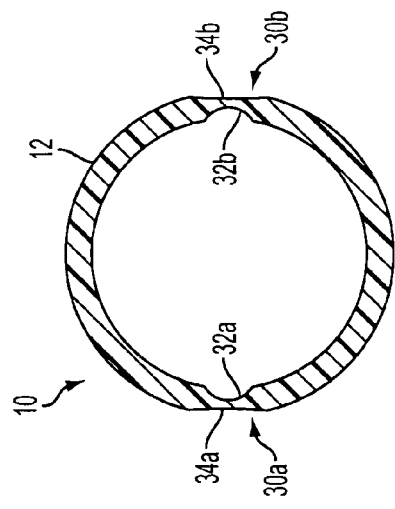
FIG. 2 is a cross-sectional view of the peel-away introducer sheath taken along line 2-2 of FIG. 1.

Referring additionally to FIGS. 2 and 3, there is illustrated in FIG. 2 a cross-sectional view of the peel-away introducer sheath taken along line 2-2 of FIG. 1 and in FIG. 3 a perspective view of an axial section of the peel-away introducer sheath taken along line 3-3 of FIG. 1. The tubular sheath 12 includes a pair of diametrically opposed peel lines 30a, 30b that extend along a longitudinal axis 38 of the sheath 12 from the proximal end 12a thereof to the distal end 12b thereof. These diametrically opposed peel lines 30a, 30b have an axially extending pitch, at least partially wrapping about the axis 38 of the sheath 12, as best seen in FIG. 1. Preferably, the axially extending pitch of the peel lines 30a, 30b is about between 5° and 45° although variations well outside this range are also contemplated. Therefore, and as shown in the illustrated embodiment of FIG. 1, each opposed peel line 30a, 30b has an axially extending pitch extending between the proximal 12a and distal 12b ends of the tubular sheath 12 relative to the longitudinal axis 38 of the sheath 12 wherein each axially extending pitch is located entirely within the upper circumferential half portion of the elongated tubular sheath.

The opposed peel lines 30a, 30b are defined by axially extending regions of reduced wall thickness. The axially extending pitch of the peel lines 30a, 30b serves to distribute the sheering forces exerted during the peeling process over a greater amount of the surface area of the sheath 12, as compared to prior art devices having straight peel lines. Hence, deviation from tearing along the peel lines 30a, 30b is prevented.

As best seen in FIG. 2, each peel line 30a, 30b is an axially extending region of reduced wall thickness preferably defined by a concave inner wall surface 32a, 32b and a corresponding concave or otherwise flattened outer wall surface 34a, 34b. Preferably, the radius of curvature of the concave inner wall surfaces 32a, 32b is greater than the radius of curvature of the concave outer wall surfaces 34a, 34b. Alternatively, the peel lines 30a, 30b may formed by perforations or any other frangible connection now known or later developed.

Referring now to FIGS. 4A-4E, cross-sectional views of alternative peel-away introducer sheath 12A-E are shown. As will be appreciated by those of ordinary skill in the pertinent art, the sheaths 12A-E utilizes similar principles to the sheath 12 described above. Accordingly, the sheaths of FIGS. 4A-E are appended with the letters A-E, respectively, and like structural elements are preceded by the numerals "1-5", respectively, to indicate like elements. The primary difference of the sheaths 12A-E in comparison to the sheath 12 is the shape of the inner walls 32a, 32b and outer walls 34a, 34b.

Figure 4A:
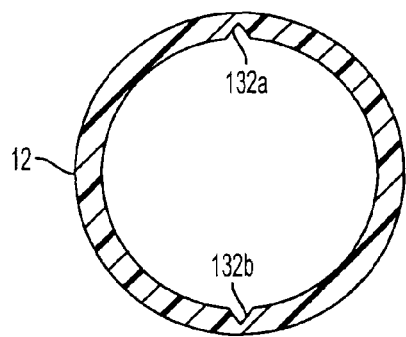
FIG. 4A is a cross-sectional view of an alternative peel-away introducer sheath constructed in accordance with a preferred embodiment of the subject technology.
Figure 4B:
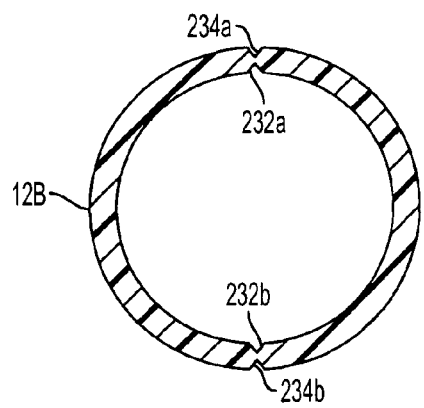
FIG. 4B is a cross-sectional view of an alternative peel-away introducer sheath constructed in accordance with a preferred embodiment of the subject technology.
Figure 4C:
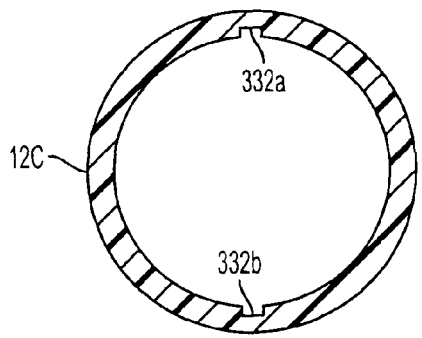
FIG. 4C is a cross-sectional view of an alternative peel-away introducer sheath constructed in accordance with a preferred embodiment of the subject technology.

In FIG. 4A, the inner walls 132a, 132b of the sheath 12A form a valley with no modification of the outer wall 134a, 134b. The valley may come to a point such as an intersection between two lines or be a rounded shape such as a semi-circle. The sheath 12B of FIG. 4B has similar valley-shaped inner walls 232a, 232b with corresponding valley-shaped outer walls 234a, 234b. As a result, the peel line can be made very thin. In FIG. 4C, the inner walls 332a, 332b of the sheath 12C form a rectangular channel with no modification of the outer wall 334a, 334b.

Figure 4D:
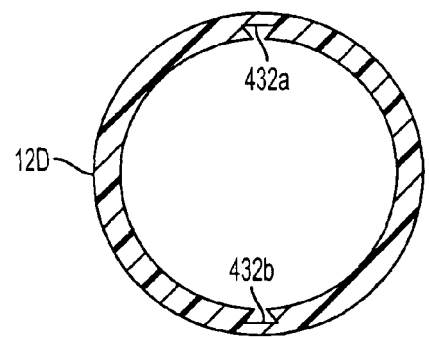
FIG. 4D is a cross-sectional view of an alternative peel-away introducer sheath constructed in accordance with a preferred embodiment of the subject technology.
Figure 4E:
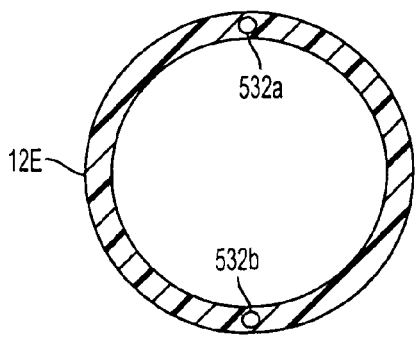
FIG. 4E is a cross-sectional view of an alternative peel-away introducer sheath constructed in accordance with a preferred embodiment of the subject technology.

In FIG. 4D, the inner walls 432a, 432b of the sheath 12D form a trapezoidal channel also with no modification of the outer wall 434a, 434b. In FIG. 4E, the peel lines of the sheath 12E are formed by axial channels intermediate the inner and outer walls 532a, 532b, 534a, 534b such that the sheath 12E may appear unmodified except in cross-sectional view. In another embodiment, the peel lines are perforated lines. It is envisioned that the various wall formations may be mixed and matched as well as combined with other variations to form a desired peel-away sheath.

In one embodiment, the tubular sheath 12 of introducer assembly 10 is formed in an extrusion process using a polymeric material, such as, for example, the Polyether Block Amide (PEBA) manufactured by Arkema under the tradename Pebax® or a similar material. During the extrusion process, the molten polymeric extrudate is forced through a die by a continuously rotating mixer such as a screw or flighted barrel. The rotating motion imparts movement that creates the pitch of the regions of reduced wall thickness, and thus the opposed peel lines 30a, 30b. The rotating motion can be controlled to vary the pitch of the peel lines 30a, 30b. For example, the rotational speed can be increased to increase the pitch of the peel lines 30a, 30b, and vice versa.

While the device and manufacturing methods of subject invention have been shown and described with reference to preferred embodiments, those skilled in the art will readily appreciate that changes and/or modifications may be made thereto without departing from the spirit and scope of the subject invention as defined by the appended claims.

What is claimed is:

1. A peel-away vascular introducer comprising:
   a) an elongated tubular sheath having opposed proximal and distal ends defining a longitudinal axis, a circumference, and a pair of diametrically opposed peel lines each having a predetermined length extending from the proximal end substantially to the distal end of the sheath, wherein each opposed peel line has an axially extending pitch extending between the proximal and distal ends of the elongated tubular sheath relative to the longitudinal axis and located entirely within a circumferential half portion of the elongated tubular sheath; and
   b) spreadable handles associated with the proximal end of the sheath for splitting the sheath along the peel lines.

2. A peel-away vascular introducer as recited in claim 1, wherein the axially extending pitch of the peel lines is between about 5° and 45° with respect to the longitudinal axis of the sheath.

3. A peel-away vascular introducer as recited in claim 1, wherein the peel lines are defined by axially extending regions of reduced wall thickness, relative to the wall thickness of a remainder of the sheath.

4. A peel-away vascular introducer as recited in claim 3, wherein each axially extending region of reduced wall thickness is defined by a concave outer wall surface and a convex inner wall surface.

5. A peel-away vascular introducer as recited in claim 4, wherein a radius of curvature of the convex inner wall surface is greater than a radius of curvature of the convex outer wall surface.

6. A peel-away vascular introducer as recited in claim 1, wherein the peel lines are defined by axially extending regions of reduced wall thickness defined by a valley inner wall surface.

7. A peel-away vascular introducer as recited in claim 1, wherein the peel lines are defined by axially extending regions of reduced wall thickness defined by a valley inner and outer wall surface.

8. A peel-away vascular introducer as recited in claim 1, wherein the peel lines are defined by axially extending regions of reduced wall thickness defined by a rectangular channel inner wall surface.

9. A peel-away vascular introducer as recited in claim 1, wherein the peel lines are defined by axially extending regions of reduced wall thickness defined by a trapezoidal inner wall surface.

10. A peel-away vascular introducer as recited in claim 1, including the elongated tubular sheath having opposed inner and outer wall surfaces with respect to a longitudinal axis of the sheath, wherein each of the peel lines are defined by an axially extending channel within the inner and outer wall surfaces of the tubular sheath.

11. A peel-away vascular introducer as recited in claim 1, further comprising a dilator accommodated within the sheath.

12. A peel-away vascular introducer comprising an elongated tubular sheath having opposed proximal and distal ends defining a longitudinal axis and a circumference, and a pair of opposing peel lines each extending from the proximal end substantially to the distal end of the sheath, wherein the opposed peel lines each has an axially extending pitch extending between the proximal and distal ends of the elongated tubular sheath relative to the longitudinal axis and located entirely within a circumferential half portion of the elongated tubular sheath.

13. A peel-away vascular introducer as recited in claim 12, further comprising spreadable handles associated with the proximal end of the sheath for splitting the sheath along the peel lines.

14. A peel-away vascular introducer as recited in claim 12, wherein the sheath is fabricated from a polyether block amide material.

* * * * *